US009674935B2

(12) United States Patent
Kuwabara et al.

(10) Patent No.: US 9,674,935 B2
(45) Date of Patent: Jun. 6, 2017

(54) RADIATION SIGNAL PROCESSING DEVICE, RADIATION IMAGING SYSTEM, AND RADIATION SIGNAL PROCESSING METHOD

(71) Applicant: FUJIFILM CORPORATION, Minato-ku, Tokyo (JP)

(72) Inventors: Takeshi Kuwabara, Kanagawa (JP); Masaru Sato, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 119 days.

(21) Appl. No.: 14/692,746

(22) Filed: Apr. 22, 2015

(65) Prior Publication Data
US 2015/0230324 A1    Aug. 13, 2015

Related U.S. Application Data

(63) Continuation of application No. PCT/JP2013/076131, filed on Sep. 26, 2013.

(30) Foreign Application Priority Data

Nov. 2, 2012  (JP) ................................. 2012-242997

(51) Int. Cl.
*H05G 1/38* (2006.01)
*H05G 1/44* (2006.01)
*A61B 6/00* (2006.01)

(52) U.S. Cl.
CPC .............. *H05G 1/44* (2013.01); *A61B 6/4233* (2013.01); *A61B 6/542* (2013.01)

(58) Field of Classification Search
CPC ......... A61B 6/548; A61B 6/4405; A61B 6/00; A61B 6/4441; A61B 6/4488;
(Continued)

(56) References Cited

U.S. PATENT DOCUMENTS

| 4,322,619 A | * | 3/1982 | Nelson | G03B 42/02 378/62 |
| 6,399,950 B1 | * | 6/2002 | Kimura | G01T 1/24 250/370.09 |
| 7,313,224 B1 | * | 12/2007 | Saunders | A61B 6/544 378/108 |

FOREIGN PATENT DOCUMENTS

CN    101254110 A    9/2008
CN    202143287 U    2/2012
(Continued)

OTHER PUBLICATIONS

English translation of the Japanese Office Action dated Apr. 26, 2016 in the corresponding Japanese Patent Application No. 2012-242997.
(Continued)

*Primary Examiner* — Irakli Kiknadze
(74) *Attorney, Agent, or Firm* — SOLARIS Intellectual Property Group, PLLC

(57) ABSTRACT

A radiation signal processing device including: a reception section that receives as a digital signal a signal representing a detection result from a radiation imaging device that captures an image according to irradiated radiation, and that detects a radiation irradiation amount and outputs the signal representing the detection result; and a conversion section that converts the digital signal representing the detection result received by the reception section into an analog signal recognizable by a radiation irradiation device that irradiates radiation onto the radiation imaging device and stops radiation irradiation in cases in which radiation has reached a specific irradiation amount.

16 Claims, 6 Drawing Sheets

(58) Field of Classification Search
CPC ....... A61B 6/4233; A61B 6/467; A61B 6/563;
A61B 6/4411; A61B 6/461; A61B 6/465;
A61B 6/469; A61B 6/542; A61B 6/544;
A61B 6/56; A61B 6/566; A61B 6/03;
A61B 6/4494; A61B 6/587; A61B 6/032;
A61B 6/08; A61B 6/4208; A61B 6/4266;
A61B 6/4283; A61B 6/547; A61B 6/586;
A61B 6/0414; A61B 6/06; H05G 1/44
USPC .............................................. 378/91, 97, 98
See application file for complete search history.

(56) References Cited

FOREIGN PATENT DOCUMENTS

| | | |
|---|---|---|
| JP | 04-105477 A | 4/1992 |
| JP | 2006-263339 A | 10/2006 |
| JP | 2008-000595 A | 1/2008 |
| JP | 2008-117641 A | 5/2008 |
| JP | 2012-073230 A | 4/2012 |

OTHER PUBLICATIONS

International Search Report issued in International Application No. PCT/JP2013/076131 on Nov. 5, 2013.
Written Opinion of the ISA issued in International Application No. PCT/JP2013/076131 on Nov. 5, 2013.
Chinese Office Action dated Feb. 20, 2017 in corresponding Chinese Patent Application No. 201380056375.3 and a Partial English Translation thereof.

* cited by examiner

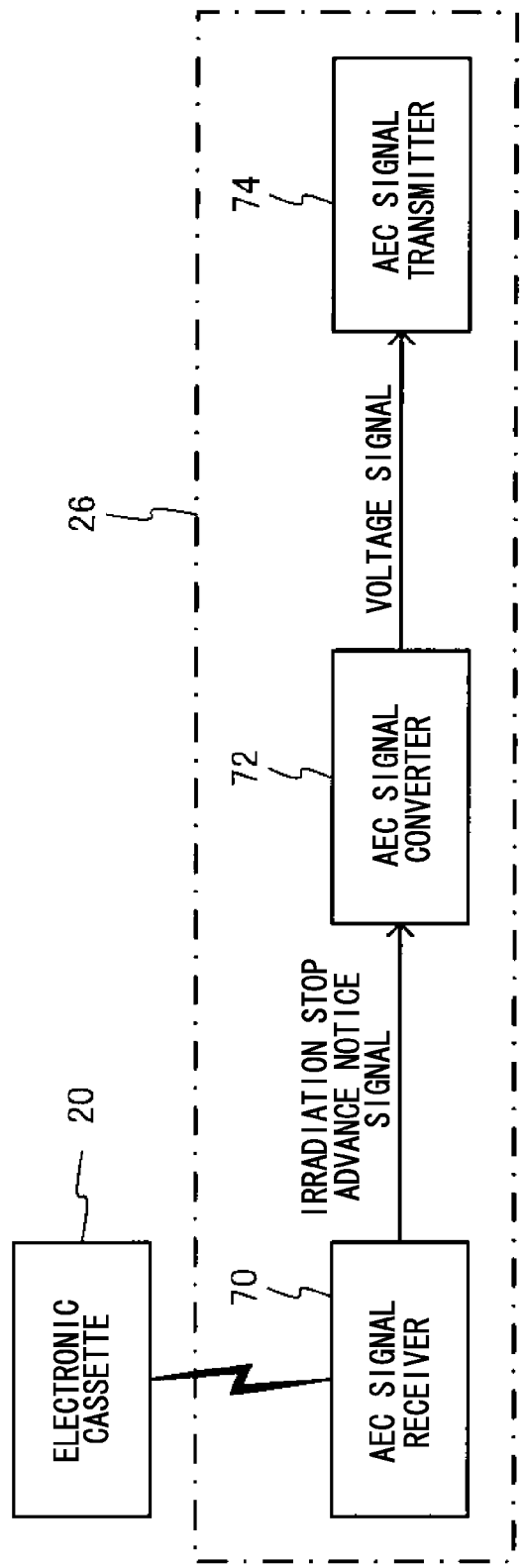

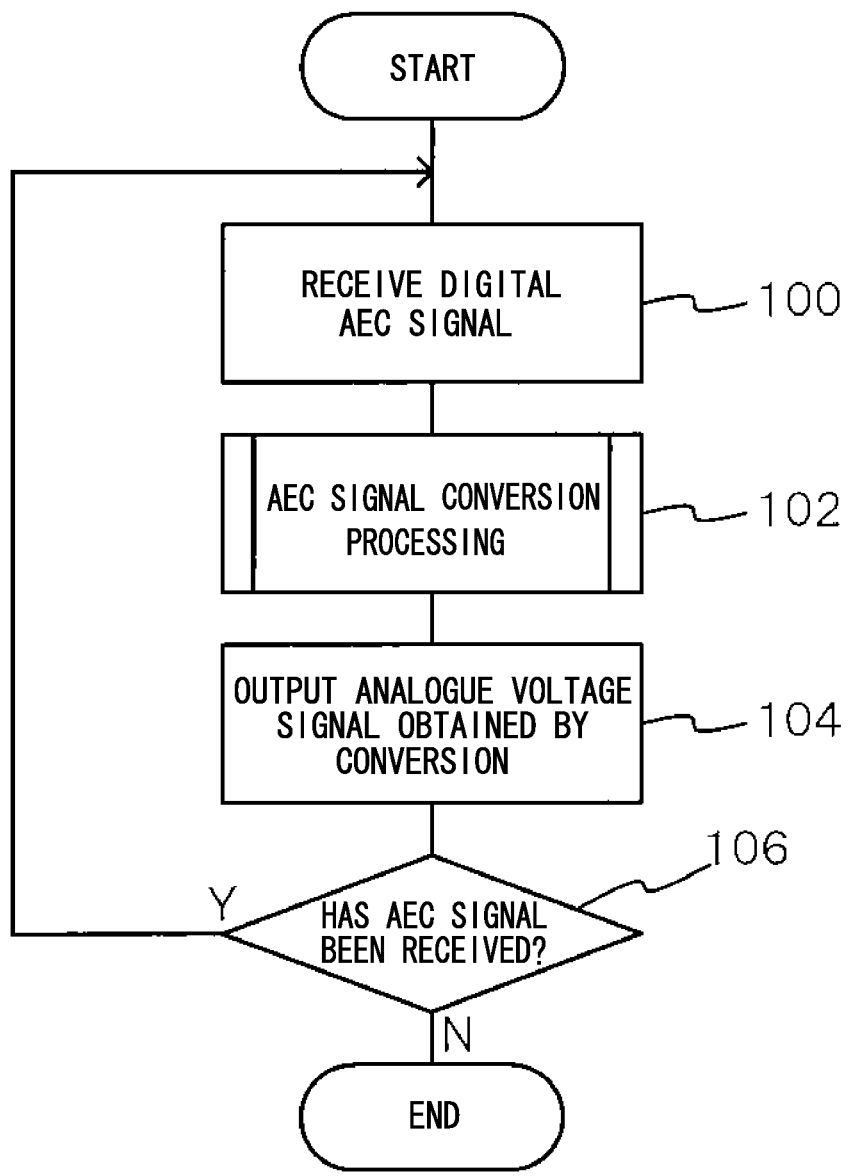

RADIATION SIGNAL PROCESSING DEVICE, RADIATION IMAGING SYSTEM, AND RADIATION SIGNAL PROCESSING METHOD

CROSS-REFERENCE TO RELATED APPLICATION

This application is a continuation application of International Application No. PCT/JP2013/076131, filed Sep. 26, 2013, the disclosure of which is incorporated herein by reference in its entirety. Further, this application claims priority from Japanese Patent Application No. 2012-242997, filed Nov. 2, 2012, the disclosure of which is incorporated herein by reference in its entirety.

FIELD

The disclosure relates to a radiation signal processing device, a radiation imaging system, and a radiation signal processing method.

BACKGROUND

Recently, radiation detectors (sometimes referred to as "electronic cassettes" or the like) such as Flat Panel Detectors (FPDs) in which a radiation sensitive layer is disposed over a Thin Film Transistor (TFT) active matrix substrate, and that are capable of converting radiation doses into digital data (electrical signals) are being put into practice. Radiographic imaging devices employing such radiation detectors, that capture radiation images expressed by irradiated radiation doses, are also being put into practice.

Such radiation imaging devices include those that monitor radiation dose in order to control starting and stopping of radiation irradiation.

For example, technology described in Japanese Patent Application Laid-Open (JP-A) No. 2008-595 detects a radiation irradiation amount and performs radiation irradiation control using an ionization chamber. In the technology described in JP-A No. 2008-595, an interface is provided between the ionization chamber and an irradiation device, receives irradiation characteristic data from the ionization chamber by wireless communication, and acts as an intermediary for the data to enable the irradiation device to determine control parameters.

In technology described in JP-A No. 2006-263339, an X-ray stop signal is transmitted to a console through a wireless relay based on an X-ray dose signal detected by an X-ray dose sensor of a cassette.

SUMMARY

An aspect of the disclosure is a radiation signal processing device of the disclosure that includes: a reception section that receives as a digital signal a signal representing a detection result from a radiation imaging device that captures an image according to irradiated radiation, and that detects a radiation irradiation amount and outputs the signal representing the detection result; and a conversion section that converts the digital signal representing the detection result received by the reception section into an analogue signal recognizable by a radiation irradiation device that irradiates radiation onto the radiation imaging device and stops radiation irradiation in cases in which radiation has reached a specific irradiation amount.

BRIEF DESCRIPTION OF DRAWINGS

FIG. 4 is a functional block diagram illustrating a schematic configuration of an AEC I/F.

FIG. 6 is a flowchart illustrating an example of a flow of processing performed by an AEC I/F of a radiation imaging system according to the present exemplary embodiment.

DETAILED DESCRIPTION OF THE INVENTION

Figure 1:
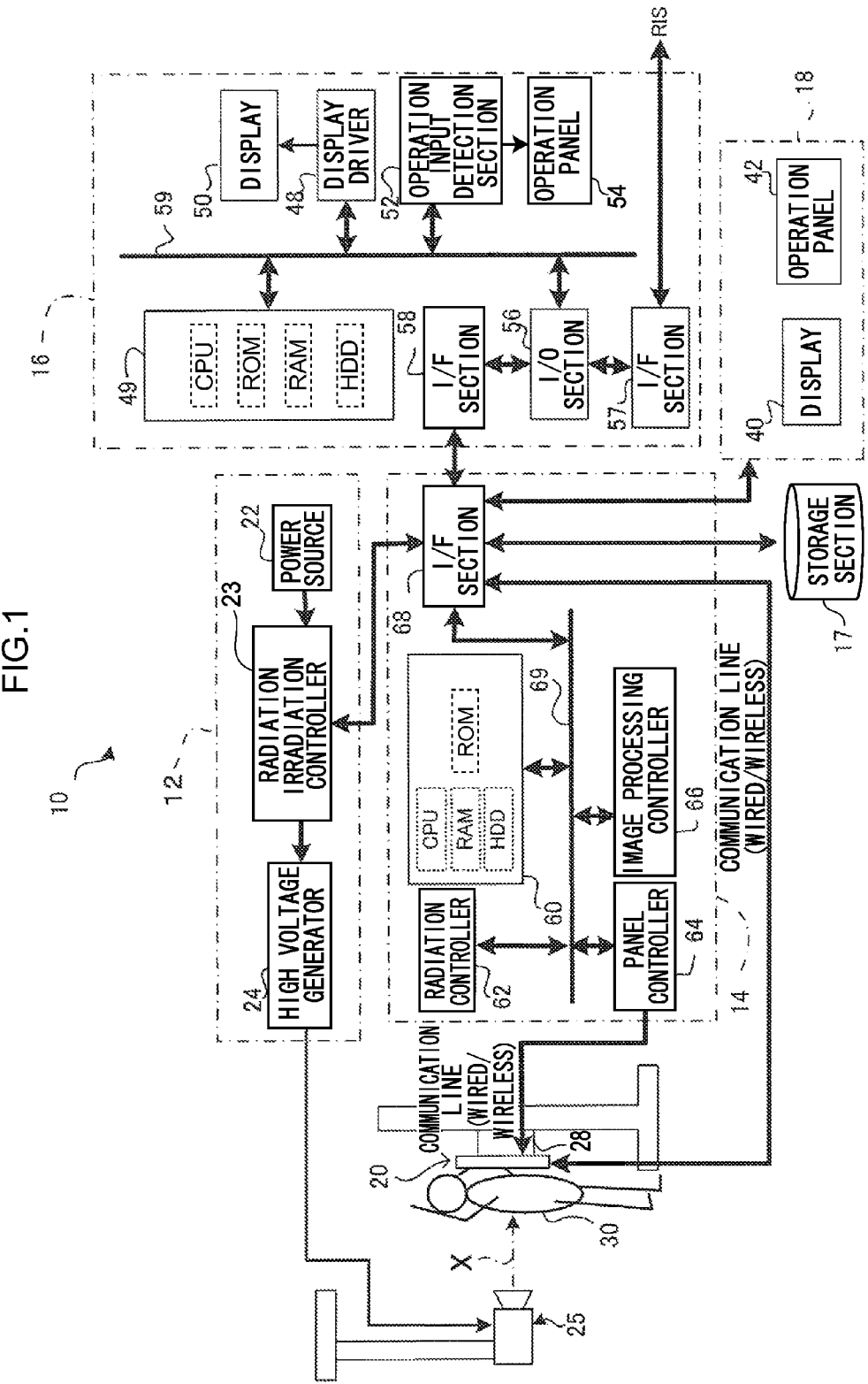
FIG. 1 is a schematic configuration diagram outlining an overall configuration of an example of a radiation imaging system of an exemplary embodiment.

Explanation follows regarding an example of an exemplary embodiment, with reference to the drawings. First, explanation is given regarding an outline configuration of an overall radiation imaging system according to the present exemplary embodiment. FIG. 1 is a schematic configuration diagram outlining the overall configuration of an example of a radiation imaging system according to the present exemplary embodiment. In a radiation imaging system 10 of the present exemplary embodiment, an electronic cassette 20 itself includes a function to detect the start of radiation irradiation (image capture start), and a function to detect radiation irradiation stop (image capture completion).

The radiation imaging system 10 of the present exemplary embodiment includes a function to perform radiation imaging based on an instruction (image capture menu) input through a console 16 from an external system (for example a Radiology Information System (RIS)), by operation by a doctor, radiologist, or the like.

Moreover, the radiation imaging system 10 according to the present exemplary embodiment includes a function to allow a doctor, radiologist, or the like, to read a radiation image by displaying a captured radiation image on a display 50 of the console 16 or on a radiation image reading apparatus 18.

The radiation imaging system 10 of the present exemplary embodiment includes a radiation generation device 12, a control device 14, a console 16, a storage section 17, a radiation image reading apparatus 18, and an electronic cassette 20.

The radiation generation device 12 includes a power source 22, a radiation irradiation controller 23, and a high voltage generator 24. The radiation irradiation controller 23 includes a function to irradiate an image capture target site of a subject 30 with radiation X from a radiation irradiation source 25, based on control of a radiation controller 62 of the control device 14. The radiation irradiation controller 23 of the present exemplary embodiment supplies a current, supplied from the power source 22, to the high voltage generator 24, and supplies a high voltage generated by the high voltage generator 24 to the radiation irradiation source 25 to generate the radiation X. Note that the power source 22 may be either an alternating current power source or a direct current power source. The high voltage generator 24 may be a single phase transformer type, a triple phase transformer type, an inverter type, or a capacitor type. FIG. 1 illustrates a fixed radiation generation device 12; however there is no limitation thereto, and the radiation generation device 12 may be a mobile type.

Figure 2:
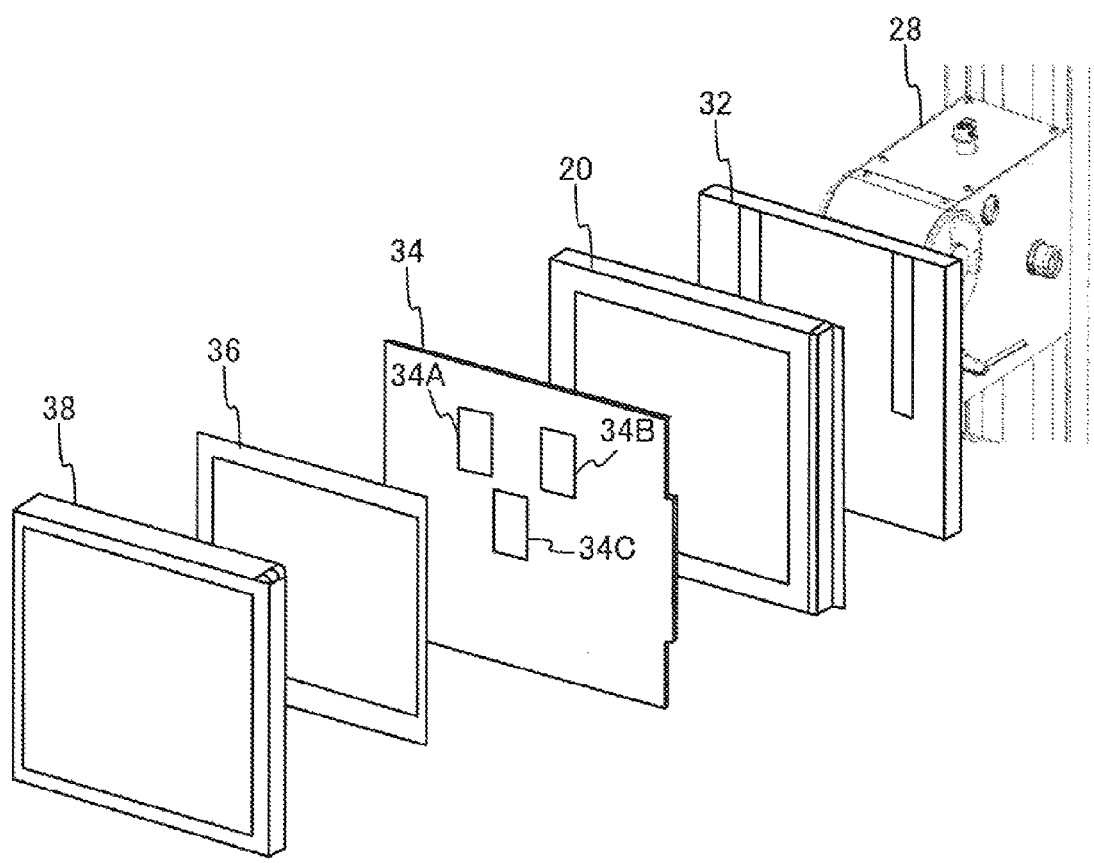
FIG. 2 is a diagram illustrating an example of an electronic cassette held in a wall stand.

The radiation X that has passed through the subject 30 irradiates the electronic cassette 20 held in a wall stand 28. As illustrated in FIG. 2, for example, the electronic cassette 20 is attached to a back face bracket 32 provided to the wall stand 28 fixed to a wall. A cover 38 is provided on the radiation irradiated side of the electronic cassette 20. An ion chamber 34 that includes plural photoreceptor regions 34A to 34C and detects a radiation irradiation amount, and a Bucky grid 36 to eliminate scattered rays, can be placed between the electronic cassette 20 and the cover 38. In the present exemplary embodiment, the electronic cassette 20 outputs not only image data expressing radiation images, but also a signal for stopping radiation irradiation, enabling stopping of the irradiation of radiation to be controlled even without the ion chamber 34, and allowing the ion chamber 34 to be omitted. Alternatively, configuration may be made so as to enable radiation irradiation to be stopped using the ion chamber 34.

The electronic cassette 20 generates charges according to the dose of radiation X that has passed through the subject 30, and includes a function to generate and output image data expressing a radiation image based on the generated charge amounts. Note that in the present exemplary embodiment, "dose" refers to the radiation intensity, and, for example, means the radiation irradiation per unit of time at a specific tube voltage and a specific tube current. FIG. 2 illustrates an example in which the electronic cassette 20 is held in the wall stand 28; however an imaging table for the subject to lie on may be provided, with the electronic cassette 20 held on the imaging table.

In the present exemplary embodiment, image data expressing radiation images output from the electronic cassette 20 are input to the console 16 through the control device 14. The console 16 includes a function to control the radiation generation device 12 and the electronic cassette 20 using imaging menus, various data, and the like, acquired from an external system (RIS) or the like via wireless communications (LAN: Local Area Network) or the like. The console 16 also includes a function to transmit and receive various data, including image data of radiation images, to and from the control device 14, and includes a function to transmit and receive various data to and from the electronic cassette 20.

The console 16 is configured as a server computer, and includes a controller 49, a display driver 48, a display 50, an operation input detection section 52, an operation panel 54, an I/O section 56, an I/F section 57, and an I/F section 58.

The controller 49 includes a function to control the operation of the console 16 overall, and includes a CPU, ROM, RAM and an HDD. The CPU includes a function to control operation of the console 16 overall. The ROM is pre-stored, for example, with various programs including a control program used by the CPU. The RAM includes a function to temporarily store various data, and the hard disk drive (HDD) includes a function to store and hold various data.

The display driver 48 includes a function to control display of various data on the display 50. The display 50 of the present exemplary embodiment includes a function to display for example an image capture menu and captured radiation images. The operation input detection section 52 includes a function to detect an operation state of the operation panel 54. The operation panel 54 is for input of operation instruction related to capturing radiation images by, for example, a doctor or radiologist. The operation panel 54 in the present exemplary embodiment is, for example, configured including a touch panel, a touch pen, plural keys and/or a mouse. Note that in cases in which the operation panel 54 is configured as a touch panel then this may be common configuration with the display 50.

The I/O section 56 and the I/F section 58 include a function to perform transmission and reception of various data to and from the control device 14 and the radiation generation device 12, and to perform transmission and reception of various data such as image data to and from the electronic cassette 20, using wireless communication or wired communication. The I/F section 57 includes a function to perform transmission and reception of various data to and from the RIS.

The controller 49, the display driver 48, the operation input detection section 52, the I/F section 58, and the I/O section 56 are connected together through a bus 59, such as a system bus, or a control bus, enabling data and the like to be mutually exchanged therebetween. The controller 49 is accordingly capable of controlling display of various data on the display 50 through the display driver 48, and of controlling transmission and reception of various data to and from the radiation generation device 12 and the electronic cassette 20 through the I/F section 58.

The control device 14 of the present exemplary embodiment includes a function to control the radiation generation device 12 and the electronic cassette 20 based on instructions from the console 16, and includes a function to control storage of radiation images received from the electronic cassette 20 on the storage section 17, and to control display on the display 50 of the console 16 and the radiation image reading apparatus 18.

The control device 14 of the present exemplary embodiment includes a system controller 60, a radiation controller 62, a panel controller 64, an image processing controller 66, and an I/F section 68.

The system controller 60 includes a function to control the control device 14 overall, and includes a function to control the radiation imaging system 10. The system controller 60 includes a CPU, ROM, RAM, and an HDD. The CPU includes a function to control the control device 14 overall and to control operation the radiation imaging system 10, and the ROM is pre-stored with various programs and the like including a control program employed by the CPU. The RAM includes a function to temporarily store various data, and the HDD includes a function to store and hold various data. The radiation controller 62 includes a function to control the radiation irradiation controller 23 of the radiation generation device 12 based on instructions from the console 16 and the like. The panel controller 64 includes a function to control the electronic cassette 20 based on instructions from the console 16 and the like. The image processing controller 66 includes a function to perform various image processing on radiation images.

The system controller 60, the radiation controller 62, the panel controller 64, and the image processing controller 66 are mutually connected together through a bus 69, such as a system bus, or a control bus, enabling data and the like to be mutually exchanged therebetween.

The storage section 17 of the present exemplary embodiment includes a function to store captured radiation images and data related to the captured radiation images. Examples of the storage section 17 include an HDD.

The radiation image reading apparatus 18 of the present exemplary embodiment is a device including a function to allow a viewer to read captured radiation images, and although not particularly limited, examples thereof include what are referred to as reader viewers and consoles. The radiation image reading apparatus 18 of the present exemplary embodiment is configured as a personal computer, and, similarly to the console 16 and the control device 14, is configured including a CPU, ROM, RAM, an HDD, a display driver, a display 40, an operation input detection section, an operation panel 42, an I/O section, and an I/F section. Note that out of these configurations, FIG. 1 only illustrates the display 40 and the operation panel 42 so as to avoid confusion.

The radiation imaging system 10 includes an Automatic Exposure Control (AEC) function to control radiation irradiation stop (referred to below as an AEC function), and to control a timing of stopping radiation irradiation from the radiation irradiation source 25 by using the radiation irradiation controller 23 to control the high voltage generator 24 based on a signal output from the electronic cassette 20. Namely, the electronic cassette 20 includes a configuration to detect a radiation irradiation amount. A dedicated sensor or the like may be provided as configuration to detect the radiation irradiation amount; however the present exemplary embodiment is one in which pixels are provided to detect the radiation irradiation amount.

Figure 3:
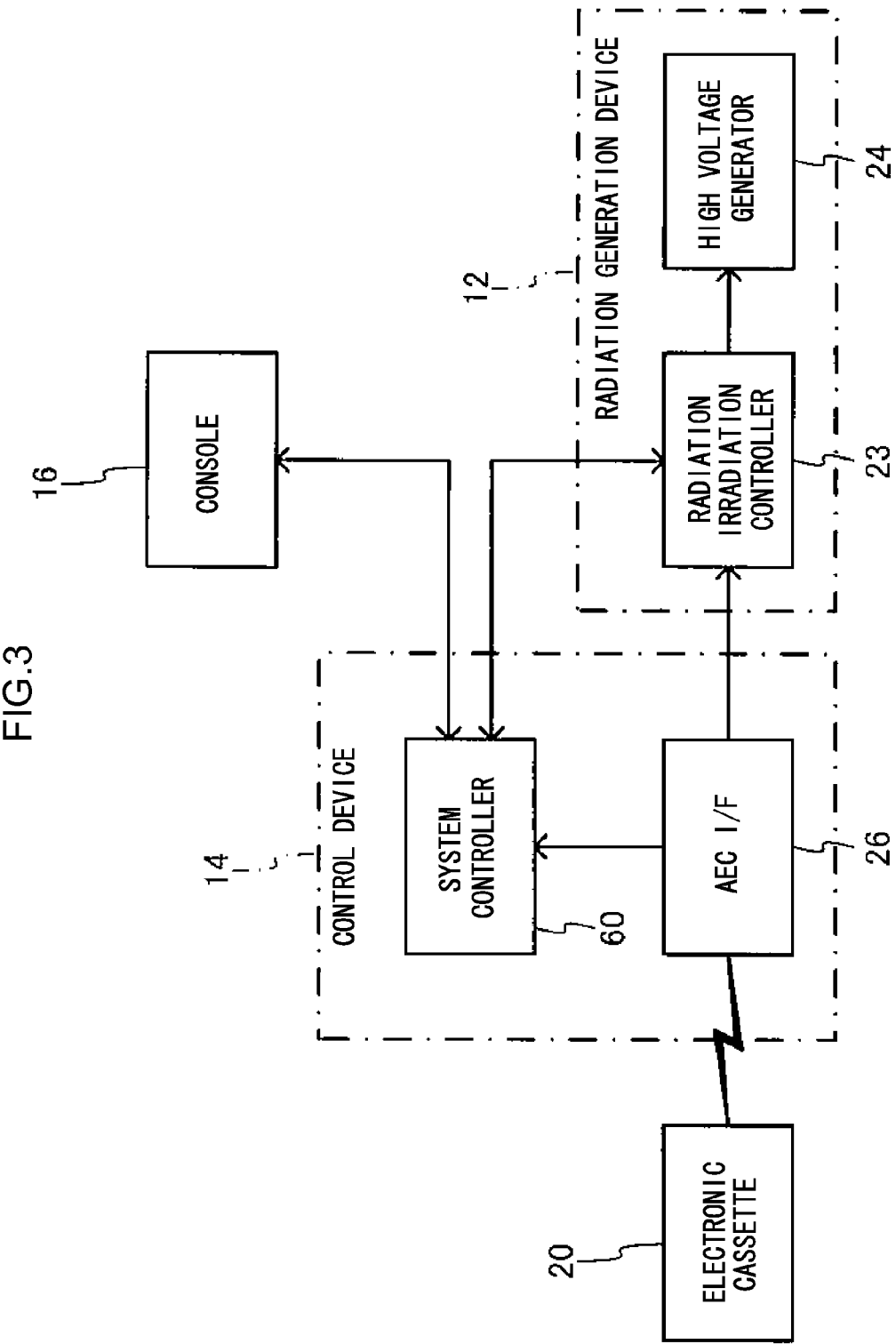
FIG. 3 is a block diagram selectively illustrating a partial configuration relating to an AEC function in a radiation imaging system according to the present exemplary embodiment.

Note that in order to perform an AEC function in a system of related technology, radiation dose is detected by an ion chamber 34 and a signal representing an analogue radiation dose is output to a radiation irradiation controller 23, and radiation irradiation is stopped by outputting a radiation irradiation stop signal to a high voltage generator 24 when the cumulative radiation dose has reached a specific value. However, in the present exemplary embodiment, the radiation irradiation amount is detected by the electronic cassette 20, and the detection result is transmitted to the control device 14 by wireless communication. The I/F section 68 of the control device 14 described above is accordingly provided with an AEC interface (I/F) 26, as illustrated in FIG. 3, in order to receive the radiation irradiation amount detection result wirelessly transmitted from the electronic cassette 20. FIG. 3 is a block diagram selectively illustrating a partial configuration relating to the AEC function of the radiation imaging system 10 according to the present exemplary embodiment.

Note that when the radiation irradiation amount detection results are received by wireless communication, there is the possibility that the signal may not arrive due to interference. The electronic cassette 20 accordingly outputs a digital irradiation stop advance notice signal. As the irradiation stop advance notice signal, the electronic cassette outputs, for example, a digital signal representing an irradiation duration t from irradiation start until the present, and a remaining irradiation duration $\Delta t$ ($=T-t$) with respect to an appropriate irradiation duration T calculated by the electronic cassette 20. The irradiation duration t from irradiation start, and the appropriate irradiation duration T are, for example, recalculated and retransmitted at 1 msec intervals (however, the precision of t and T is, for example, increments of 0.1 msec), enabling radiation to be stopped as long as the receiving side is able to receive the signal on a single occasion, thereby reducing the risk of overexposure. More precise dose stoppage is possible due to updating with the most recent of the repeatedly received signals.

In order to make use of the radiation irradiation stop control using the ion chamber 34 in the related technology, in the present exemplary embodiment, the AEC I/F 26 includes a function to convert the signal (stop advance notice signal) for controlling radiation irradiation stop obtained from the electronic cassette 20 into an analogue signal of the format employed in the related technology. Outputting the analogue signal converted by the AEC I/F 26 to the radiation generation device 12 enables radiation irradiation stop to be controlled. The AEC I/F 26 has a wired connection to the radiation generation device 12 to prevent radiation irradiation stop from being impeded by interference. The electronic cassette 20 may also have a wired connection to the AEC I/F 26.

Specifically, as illustrated in FIG. 4, the AEC I/F 26 includes an AEC signal receiver 70, an AEC signal converter 72, and an AEC signal transmitter 74. FIG. 4 is a functional block diagram illustrating a schematic configuration of the AEC I/F 26.

The AEC signal receiver 70 receives the digital irradiation stop advance notice signal wirelessly transmitted from the electronic cassette 20, and outputs the received digital irradiation stop advance notice signal to the AEC signal converter 72.

The AEC signal converter 72 converts the digital irradiation stop advance notice signal into an analogue unit voltage increase signal and integrates this signal with respect to time to derive an analogue signal (voltage signal) representing a voltage corresponding to the radiation irradiation amount detected by the electronic cassette 20, and outputs the analogue signal (voltage signal) to the AEC signal transmitter 74.

The AEC signal transmitter 74 outputs the analogue signal (voltage signal) obtained by conversion in the AEC signal converter 72 to the radiation irradiation controller 23 of the wire-connected radiation generation device 12. The radiation irradiation controller 23 is thereby input with the analogue signal representing a voltage corresponding to the radiation irradiation amount, similarly to in the related technology, enabling the radiation irradiation stop system of the related technology to be used to perform radiation irradiation until the radiation irradiation amount has reached an appropriate irradiation amount.

Detailed explanation now follows regarding conversion of the digital irradiation stop advance notice signal to the analogue signal in the AEC signal converter 72 of the AEC I/F 26.

First, an irradiation start time is denoted 0, and irradiation stop advance notice signal pairs transmitted from the electronic cassette 20 are denoted (t1, $\Delta$t1), (t2, $\Delta$t2), (t3, $\Delta$t3), and so on. Note that supplementary data other than the irradiation stop advance notice signal (such as an identifier ID or an error code) may also be transmitted.

Figure 5A:
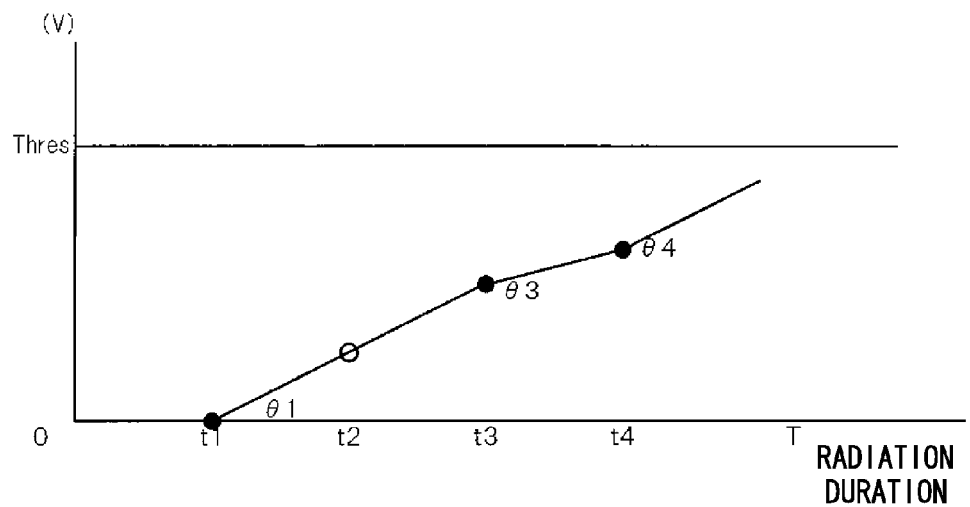
FIG. 5A is a diagram to explain conversion from a digital irradiation stop advance notice signal to an analogue signal.

For example, a voltage increase $\theta$ is computed as below in a case in which, for an irradiation duration from irradiation start until the present moment, reception of t1 was successful, reception of t2 failed, and reception of t3 and t4 were successful. Note that in FIG. 5A, the black circles indicate successful reception, and the white circles indicate reception failure.

$\theta 1 = \text{Thres}/\Delta t1$ $\theta 2 =$ not calculated, as reception failed $\theta 3 = (\text{Thres} - \theta 1 \times (t3 - t1))/\Delta t3$ $\theta 4 = (\text{Thres} - \theta 1 \times (t3 - t1) - \theta 3 \times (t4 - t3))/\Delta t4$ Namely, an amount is derived by dividing a remaining quantity by the remaining duration, and this amount is output as a unit voltage increase signal of the voltage increase $\theta$ (V/sec) per a unit of time that is the same as that of the AEC of related technology. Namely, the voltage increase θ is integrated with respect to time, and stopping is performed once the integrated amount reaches Thres. Converting the irradiation stop advance notice signal into an analogue signal in this manner enables the voltage increase θ to be derived from a single occasion, even when the signal is not received on two occasions, enabling conversion to an analogue signal even when the wireless connection is prone to cutting out, as long as reception can be made on a single occasion.

Note that in cases in which the radiation dose becomes large and immediate stoppage is to be performed, immediate stoppage is performed with θ=maximum due to outputting Δt=0 from the electronic cassette 20.

Thres in the above calculations indicates a threshold value of the appropriate irradiation duration T, and is adjusted during installation or maintenance of the radiation generation device 12 such that, similarly to the AEC of related technology, stoppage occurs at a specific output under a uniform exposure. So doing enables a given (digit) at which to stop the electronic cassette 20 to be associated with a given (V) at which to stop the radiation irradiation controller 23. For example, the Thres (V) is taken as the Th (digit) of the electronic cassette 20.

Due to dose stability, and limitations to the precision dose detection and computation, T=t−Δt is not necessarily constant during repeated transmission. Due to changing in a manner such as T1, T1, T3, and so on, it is not necessarily the case in the above equation that t3−t1=Δt1−Δt3. Precision is therefore raised by always updating the slope using the most recently received data.

The power of ten of the absolute value of the irradiation duration t varies by image capture scene due to, for example, being immediately after irradiation start, being immediately prior to completion, and imaging subject (thickness). However, the number of bits taken should not be too large in order to secure reliable wireless transmission. Accordingly, the irradiation stop advance notice signal incorporates a unit of time such as (t, Δt, unit), thereby enabling the number of digits used to express the irradiation duration t and the remaining irradiation duration Δt to be suppressed to a fixed number of digits, whether the irradiation duration is long or short. The bit length of the irradiation stop advance notice signal can accordingly be kept to a minimum, reducing the cycle for repeating transmission.

Figure 5B:
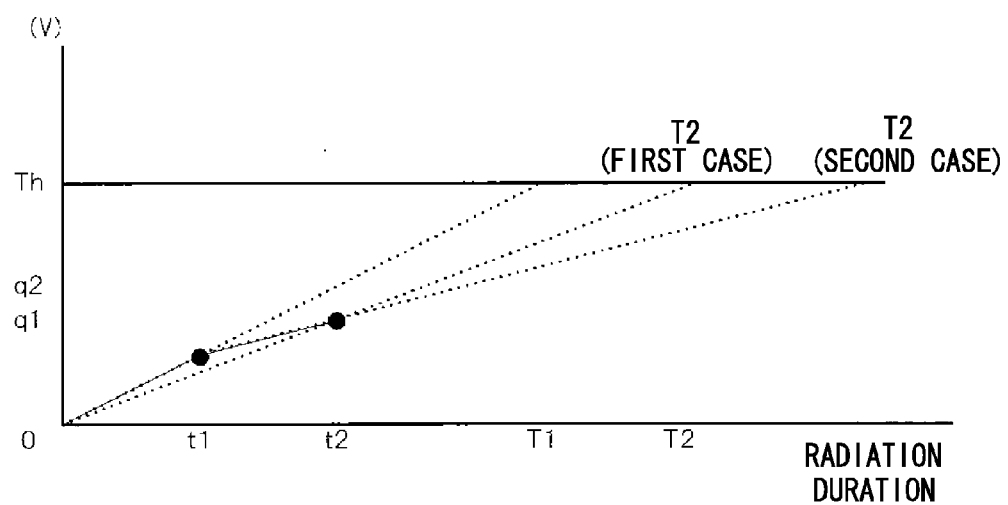
FIG. 5B is a diagram to explain a method of deriving $\Delta t$ or T.

Explanation follows regarding an equation for deriving the remaining irradiation duration Δt or the appropriate irradiation duration T. FIG. 5B is a diagram to explain derivation of the remaining irradiation duration Δt or the appropriate irradiation duration T.

Note that t is the time from irradiation start, and is therefore a known value. Th is adjusted during installation or maintenance of the radiation generation device 12, similarly to the threshold value Thres described above, and is adjusted so as to stop at a specific output at a constant uniform exposure, similarly to the AEC of related technology, and is therefore a known value. Integrated pixel values q(digit) at respective points in time are detection values of the electronic cassette 20, and are therefore also known values.

For example, in the example of FIG. 5B, since there has been an increase to q1 (digit) by t1 seconds, the time T until Th(digit) will be reached at this pace is expressed by the following equation:

$$T1/t1 = Th/q1,$$

therefore $$T1 = (Th/q1) \times t1$$

There are various methods by which T2 can be determined, of which two are described here. First, as a first case, T1 is derived in the same manner from the most up-to-date total integration amount q2 and the most up-to-date total irradiation duration t2, giving:

$$T2 = (Th/q2) \times T2$$

In another method (a second case), the amount of change from t1 to t2 is calculated. This case employs the following equation.

$$(T2-t1)/(t2-t1) = (Th-q1)/(q2-q1),$$

therefore $$T2 = t1 + (Th-q1) \times (t2-t1)/(q2-q1)$$

T3, T4 and so on may be derived similarly. An update is performed each time, since, unlike on the AEC I/F 26 side, there is no data loss due to wireless connection interruption on the electronic cassette 20 side.

Note that methods also exist in which the voltage increase θ is calculated on the electronic cassette 20 side rather than on the AEC I/F 26 side. However, for cases in which the voltage increase θ is calculated on the electronic cassette 20 side, there is no way to correct the slope if some of the wireless communication fails to arrive, since calculation is not performed on the AEC I/F 26 side, and error therefore increases, hence the voltage increase θ is preferably calculated on the AEC I/F 26 side.

Methods also exist for calculating the appropriate irradiation duration T on the AEC I/F 26 side rather than on the electronic cassette 20 side, and, in such cases, it would be sufficient just to send pairs of pixel value q and irradiation duration t. Such a method enables constant correction of the slope. In such cases, it is easier to consider a configuration that splits dealing with pixel values (digit) and time to the electronic cassette 20 side, and dealing with voltage and time to the AEC I/F 26 side.

Next, explanation follows regarding specific processing performed by the AEC I/F 26 of the radiation imaging system 10 according to the present exemplary embodiment configured as described above. FIG. 6 is a flowchart illustrating an example of a processing flow performed by the AEC I/F 26 of the radiation imaging system 10 according to the present exemplary embodiment.

At step 100, a digital AEC signal is received from the electronic cassette 20, and processing transitions to step 102. Namely, the AEC signal receiver 70 receives the digital irradiation stop advance notice signal output from the electronic cassette 20.

At step 102, the AEC signal converter 72 performs processing (AEC signal conversion processing) to convert the digital irradiation stop advance notice signal into an analogue signal representing a radiation dose, and processing transitions to step 104. Namely, as described above, processing is performed to convert the digital irradiation stop advance notice signal representing the irradiation duration t from irradiation start until the present moment, and the remaining irradiation duration Δt (=T−t) with respect to the appropriate irradiation duration T calculated by the electronic cassette 20, into the analogue voltage increase θ per unit of time (V/sec). The derived voltage increase θ per unit of time is then integrated with respect to time to derive an analogue signal representing a voltage corresponding to the radiation irradiation amount, and processing transitions to step 104.

At step 104, the converted analogue signal (voltage signal) is output to the radiation irradiation controller 23 of the radiation generation device 12, and processing transitions to step 106. This thereby enables radiation irradiation to be stopped by the radiation irradiation controller 23 in cases in which the radiation irradiation amount has reached the specific amount, similarly to in the AEC of related technology.

At step 106, determination is made as to whether or not the AEC signal has been received, and processing returns to step 100 and repeats the above processing in cases in which determination is affirmative. The processing routine is ended in cases in which determination is negative. In this determination, determination is made as to whether or not the next AEC signal has been received, however depending on the state of the wireless connection, sometimes the next AEC signal will not have been received even though an irradiation stop dose has not yet been reached, and so standby is performed until the next AEC signal is received in cases in which the voltage increase θ per unit of time has not reached the threshold value Thres. Moreover, error processing (such as error notification) may be performed in cases in which an elapsed period during which the next AEC signal is not been received reaches a predetermined period or greater, even though the threshold value Thres has not been reached.

In the radiation imaging system 10 according to the present exemplary embodiment, the AEC I/F 26 converts the digital irradiation stop advance notice signal output from the electronic cassette 20 into an analogue signal representing dose and outputs the analogue signal in this manner. This thereby enables supplementary estimations to be made for the gaps in fragmented dose data that has been received haphazardly through wireless communication, enabling the precision of irradiation stop to be improved. Namely, irradiation stop has good precision due to being able to prevent cases in which the required cumulative value has already been exceeded in cases in which irradiation amount data is subsequently received.

The electronic cassette 20 can be employed with an unmodified system that performs AEC control using the ion chamber 34 of related technology or the like. Since a system of related technology can be used, a cassette of related technology can be employed when unable to use the electronic cassette 20 due to malfunction or the like.

Namely, since interfaces that accept analogue signals are often present on the radiation generation device side, converting to analogue signals using the AEC I/F 26, as in the present exemplary embodiment, enables connection to various types of radiation generation devices, and enables the electronic cassette 20 that detects radiation irradiation amounts to be applied to systems of related technology.

The lower the regularity of transmission of irradiation stop advance notice signals sent from the electronic cassette 20, the smaller the communication load imposed on the network environment. A smaller communication load section that delays in wireless communication are less liable to occur on each occasion, with the major advantage of stabilizing system quality. However, with a configuration for controlling exposure using a digital AEC signal of related technology, the potential excess amount on occasions in which the cumulative amount is exceeded at a given timing becomes greater the lower the regularity of transmission. By converting to an analogue signal as in the present exemplary embodiment, the excess amount can be minimized while suppressing the regularity of transmission and stabilizing communication quality.

In the present exemplary embodiment, the AEC I/F 26 converts the digital irradiation stop advance notice signal into an analogue signal representing a voltage corresponding to the radiation irradiation amount (voltage signal); however configuration may be made such that the AEC I/F 26 converts to an analogue signal representing a current corresponding to the irradiation amount (current signal).

Moreover, there are no particular limitations to the radiation in the present exemplary embodiment, and for example X-rays and gamma rays may be applied.

The processing illustrated by the flowchart for the exemplary embodiment described above may be stored and distributed as a program on various recording media.

The configuration and operation of the radiation imaging system 10, the radiation generation device 12, and the electronic cassette 20 described in the present exemplary embodiment are merely examples thereof, and modifications may be made as circumstances dictate within a range not departing from the spirit of the disclosure.

Transmission of a detection result of an irradiation amount of radiation using wireless communication has been proposed, as in the technology of JP-A No. 2008-595 and JP-A No. 2006-263339. However, using wireless communication involves the exchange of digital signals in order to pass on detection results without error. When determination as to whether or not to stop irradiation based on a cumulative irradiated radiation amount is performed on the side of a radiation generation device, the radiation imaging device side transmits data of the detected irradiated radiation dose to the radiation generation device side continuously throughout a period of radiation irradiation. When exchanging digital signals wirelessly, obviously reception can be temporarily interrupted if the strength of the wireless connection is unstable. This results in chronologically intermittent data reception on the radiation generation device side. However, with chronologically intermittent data, for example, it is not known to what extent the value of the cumulative irradiation amount has increased in a missing interval from a given timing of irradiation amount data reception, until the next timing of irradiation amount data reception. Accordingly, a required cumulative value may already have been exceeded when the irradiation amount data is received at the next timing.

Systems of related technology that detect a radiation irradiation amount using an ionization chamber and perform radiation irradiation stop control often include interfaces for receiving analogue signals, and hitherto, it has not been possible to incorporate digital signals into such systems without modification.

In consideration of the above circumstances, an object of the disclosure is to enable precise radiation irradiation stop control in a system that performs wireless radiation irradiation stop control.

An aspect of the disclosure is a radiation signal processing device of the disclosure that includes: a reception section that receives as a digital signal a signal representing a detection result from a radiation imaging device that captures an image according to irradiated radiation, and that detects a radiation irradiation amount and outputs the signal representing the detection result; and a conversion section that converts the digital signal representing the detection result received by the reception section into an analogue signal recognizable by a radiation irradiation device that irradiates radiation onto the radiation imaging device and stops radiation irradiation in cases in which radiation has reached a specific irradiation amount.

According to the radiation signal processing device of the disclosure, the reception section receives, as the digital signal, the signal representing a radiation irradiation amount detection result from the radiation imaging device.

The conversion section then converts the digital signal representing the detection result received by the reception section into the analogue signal recognizable by the radiation irradiation device. Namely, conversion by the conversion section enables radiation irradiation stop control to be performed with good precision in a system that performs wireless radiation irradiation stop control. Moreover, radiation irradiation stop control is also enabled when a radiation imaging device capable of detecting a radiation irradiation amount is employed in a system that performs radiation irradiation stop control using an ionization chamber or the like.

Configuration may be made such that the reception section receives the digital signal by wireless communication, and the conversion section further outputs the analogue signal to the radiation irradiation device connected by wire.

Configuration may also be made such that the reception section receives, as the digital signal, an irradiation stop advance notice signal representing an irradiation duration from radiation irradiation start, and a remaining irradiation duration with respect to a predetermined appropriate irradiation duration, or such that the reception section receives, as the digital signal, an irradiation stop advance notice signal representing an irradiation duration from radiation irradiation start, a remaining irradiation duration with respect to a predetermined appropriate irradiation duration, and a unit of time.

Configuration may also be made such that the conversion section performs conversion to an analogue signal representing a voltage corresponding to a radiation irradiation amount by deriving a voltage increase θ per unit of time from the digital signal and by integrating with respect to time. In such a configuration, signal precision can be increased by configuring the conversion section to derive the voltage increase θ per unit of time based on the digital signal that is most recent.

Configuration may also be made such that, in cases in which dose becomes large and immediate stoppage is to be performed, the radiation imaging device transmits as the digital signal the irradiation stop advance notice signal with the voltage increase at a maximum.

A radiation imaging system may be configured including a radiation imaging device that includes a function to detect and output a dose of irradiated radiation, and that performs capture of a radiation image, and the radiation signal processing device described above.

A signal processing method for a radiation imaging device of the disclosure, the signal processing method including: by a reception section, receiving as a digital signal a signal representing a detection result from a radiation imaging device that captures an image according to irradiated radiation, and that detects a radiation irradiation amount and outputs the signal representing the detection result; and, by a conversion section, converting the received digital signal representing the detection result into an analogue signal recognizable by a radiation irradiation device that irradiates radiation onto the radiation imaging device and stops radiation irradiation in cases in which radiation has reached a specific irradiation amount.

According to the signal processing method for a radiation imaging device of the disclosure, the reception section receives as a digital signal a signal representing the radiation irradiation amount detection result from the radiation imaging device.

The digital signal representing the received detection result is then converted into an analogue signal recognizable by the radiation irradiation device. Namely, conversion enables radiation irradiation stop control to be performed with good precision in a system that performs wireless radiation irradiation stop control. Moreover, radiation irradiation stop control is also enabled when a radiation imaging device capable of detecting a radiation irradiation amount is employed in a system that performs radiation irradiation stop control using an ionization chamber or the like.

Configuration may be made such that the digital signal is received by wireless communication, and the analogue signal is further output to the radiation irradiation device connected by wire.

Configuration may also be made to receive, as the digital signal, an irradiation stop advance notice signal representing an irradiation duration from radiation irradiation start, and a remaining irradiation duration with respect to a predetermined appropriate irradiation duration, and configuration may also be made to receive as the digital signal an irradiation stop advance notice signal representing an irradiation duration from radiation irradiation start, a remaining irradiation duration with respect to a predetermined appropriate irradiation duration, and a unit of time.

Configuration may also be made such that conversion to an analogue signal representing a voltage corresponding to a radiation irradiation amount is performed by deriving a voltage increase θ per unit of time from the digital signal and by integrating with respect to time. In such a configuration, signal precision can be increased by deriving the voltage increase θ per unit of time based on the digital signal that is most recent.

Configuration may also be made such that in cases in which dose becomes large and immediate stoppage is to be performed, the radiation imaging device transmits as the digital signal the irradiation stop advance notice signal with the voltage increase at a maximum.

The disclosure may be configured by a recording medium stored with a program that causes a computer to execute the radiation signal processing method described above.

As described above, the disclosure exhibits the excellent advantageous effect of enabling radiation irradiation stop control when a radiation imaging device capable of detecting a radiation irradiation amount is employed in a system of related technology that performs radiation irradiation stop control using an ionization chamber or the like.

Note that the disclosure of Japanese Patent Application No. 2012-242997 is incorporated in its entirety by reference herein. All cited documents, patent applications and technical standards mentioned in the present specification are incorporated by reference in the present specification to the same extent as if the individual cited document, patent application, or technical standard was specifically and individually indicated to be incorporated by reference.

The invention claimed is:

1. A radiation signal processing device, comprising:
    a reception section that captures an image according to irradiated radiation, detects a radiation irradiation amount, and receives, via wireless communication, a digital signal representing an irradiation termination advance notice signal of the radiation as a detection result of detecting the radiation irradiation amount; and
    a conversion section that converts the digital signal representing the detection result received by the reception section into an analogue signal recognizable by a radiation irradiation device that irradiates radiation at the radiation imaging device and terminates radiation irradiation in cases in which radiation has reached a specific irradiation amount.

2. The radiation signal processing device of claim 1, wherein:
the conversion section further outputs the analogue signal to the radiation irradiation device, with which the conversion section has a wired connection.

3. The radiation signal processing device of claim 1, wherein the irradiation termination advance notice signal is a signal representing an irradiation duration from radiation irradiation initiation and a remaining irradiation duration with respect to a predetermined appropriate irradiation duration.

4. The radiation signal processing device of claim 3, wherein the conversion section effects conversion to an analogue signal representing a voltage corresponding to a radiation irradiation amount by deriving a voltage increase per unit of time from the digital signal and by integrating with respect to time.

5. The radiation signal processing device of claim 4, wherein the conversion section derives the voltage increase per unit of time based on the digital signal that is most recent.

6. The radiation signal processing device of claim 4, wherein, in cases in which a dose becomes large and immediate termination is to be performed, the radiation imaging device transmits, as the digital signal, the irradiation termination advance notice signal with the voltage increase at a maximum.

7. The radiation signal processing device of claim 1, wherein the irradiation termination advance notice signal is a signal representing an irradiation duration from radiation irradiation initiation, a remaining irradiation duration with respect to a predetermined appropriate irradiation duration, and a unit of time.

8. A radiation imaging system comprising:
a radiation imaging device that includes a function of detecting and outputting a dose of irradiated radiation, and that performs imaging of a radiation image; and
the radiation signal processing device of claim 1.

9. A radiation signal processing method, comprising:
(a) by a reception section, capturing an image according to irradiated radiation, detecting a radiation irradiation amount, and receiving, via wireless communication, a digital signal representing an irradiation termination advance notice signal of the radiation as a detection result of detecting the radiation irradiation amount; and
(b) by a conversion section, converting the digital signal representing the detection result received at (a) into an analogue signal recognizable by a radiation irradiation device that irradiates radiation at the radiation imaging device and terminates radiation irradiation in cases in which radiation has reached a specific irradiation amount.

10. The radiation signal processing method of claim 9, wherein:
at (b), the analogue signal is further output to the radiation irradiation device, with which the conversion section has a wired connection.

11. The radiation signal processing method of claim 9, wherein at (a), the irradiation termination advance notice signal represents an irradiation duration from radiation irradiation initiation and a remaining irradiation duration with respect to a predetermined appropriate irradiation duration.

12. The radiation signal processing method of claim 11, wherein at (b), conversion is made to an analogue signal representing a voltage corresponding to a radiation irradiation amount by deriving a voltage increase per unit of time from the detection result and by integrating with respect to time.

13. The radiation signal processing method of claim 12, wherein the conversion section derives the voltage increase per unit of time based on the digital signal that is most recent.

14. The radiation signal processing method of claim 12, wherein in cases in which a dose becomes large and immediate termination is to be performed, the irradiation termination advance notice signal, with the voltage increase at a maximum, is transmitted as the digital signal.

15. The radiation signal processing method of claim 9, wherein at (a), the irradiation termination advance notice signal represents an irradiation duration from radiation irradiation initiation, a remaining irradiation duration with respect to a predetermined appropriate irradiation duration, and a unit of time.

16. A non-transitory computer readable recording medium storing a program that is executable to cause a computer to perform radiation signal processing, the radiation signal processing comprising:
(a) capturing an image according to irradiated radiation, detecting a radiation irradiation amount, and receiving, via wireless communication, a digital signal representing an irradiation termination advance notice signal of the radiation as a detection result of detecting the radiation irradiation amount; and
(b) converting the digital signal representing the detection result received at (a) into an analogue signal recognizable by a radiation irradiation device that irradiates radiation at the radiation imaging device and terminates radiation irradiation in cases in which radiation has reached a specific irradiation amount.

* * * * *